United States Patent [19]

Shinyama et al.

[11] Patent Number: 5,888,964
[45] Date of Patent: Mar. 30, 1999

[54] METHOD FOR INCREASING PLACENTAL BLOOD FLOW

[75] Inventors: Hiroshi Shinyama; Toshiaki Akira; Takeshi Uchida; Masahiro Watanabe, all of Hirakata, Japan

[73] Assignees: The Green Cross Corporation, Osaka; Hoechst Japan Limited, Tokyo, both of Japan

[21] Appl. No.: 637,288

[22] Filed: Apr. 24, 1996

[30] Foreign Application Priority Data

Apr. 28, 1995 [JP] Japan ..................................... 7-105656

[51] Int. Cl.$^6$ ........................... A61K 38/14; A61K 38/36
[52] U.S. Cl. ..................... 514/2; 514/8; 514/21; 514/822; 514/929
[58] Field of Search ............................. 514/2, 8, 21, 822, 514/929

[56] References Cited

FOREIGN PATENT DOCUMENTS 07316072 12/1995 Japan .

OTHER PUBLICATIONS

Shinyama et al., Jap. J. of Pharm. 68th Annual Mtg of Japanese Pharmacological Society, Nagoya Japan Mar. 25–28, 1995 vol. 67 Apr. 11, 1995 p. 278 P No. P3 126.
JP 07316072 Abstract in English.
Moe, Anticoag. Ther. & Perinatal Death vol. 59 No. 4 Apr. 1982 pp. 481–483.
Valcamonico et al, J. Perinat. Med. vol. 21 (May 1993) pp. 235–240.

*Primary Examiner*—Cecilia J. Tsang
*Assistant Examiner*—Bennett Celsa
*Attorney, Agent, or Firm*—Sughrue, Mion, Zinn, Macpeak & Seas, PLLC

[57] ABSTRACT

A method for increasing the placental blood flow, which comprises administering a human-originated antithrombin-III. The human-originated antithrombin-III increases the placental blood flow in mammals and particularly improves intrauterine growth retardation caused by a decreased blood flow. The method is highly safe to the mother and fetus, since it uses human-originated AT-III as an active ingredient, thereby enabling effective and safe treatment of intrauterine growth retardation (IUGR) and the like.

2 Claims, 1 Drawing Sheet

METHOD FOR INCREASING PLACENTAL BLOOD FLOW

TECHNICAL FIELD OF THE INVENTION

The present invention relates to a method for increasing the placental blood flow by the use of a human-originated antithrombin-III (hereinafter to be referred to as AT-III) as an active ingredient.

BACKGROUND ART

AT-III is one kind of glycoproteins belonging to $\alpha_2$-globurin present in blood plasma and has a molecular weight of 65,000–68,000. It has an inhibitory activity on blood coagulating protease and strongly inhibits coagulative activity of thrombin.

In addition, AT-III has, besides inhibitory activity on thrombin, an inhibitory activity on other coagulation factors such as activated X factor and activated IX factor. It has been reported that AT-III has an inhibitory activity on plasmin and trypsin. These inhibitory activities are known to generally proceed more quickly in the presence of heparin.

AT-III having such pharmacological action is used for the correction of abnormally enhanced coagulation, specifically for the therapy of disseminated intravascular coagulation (DIC).

It has been considered that a reduced placental blood flow is responsible for intrauterine growth retardation (IUGR) observed in gestosis, exerting detrimental effects on fetus. However, a medicament or a method for increasing the decreased placental blood flow has not been found. As a result, the means for protecting the fetus has been the separation of the fetus from the mother, namely, cesarean section.

SUMMARY OF THE INVENTION

It is therefore an object of the present invention to provide a method for treating the above-mentioned diseases, without cesarean section, whereby to achieve the normal growth of the fetus in the body of its mother.

As a result of the intensive studies done by the present inventors, it has been found for the first time that AT-III used for the correction of abnormally enhanced coagulation can increase the decreased placental blood flow without exerting harmful influence on mother or fetus.

Accordingly, the present invention relates to the following (1) to (10):

(1) a method for increasing the placental blood flow, which comprises administering a human-originated antithrombin-III, (2) the method of (1) above, wherein the human-originated antithrombin-III is administered in a dose of 1–1,000 units/kg body weight/day, (3) the method of (1) above, comprising administering the human-originated antithrombin-III to a patient with a disease accompanying a decreased placental blood flow, (4) the method of (2) above, comprising administering the human-originated antithrombin-III to a patient with a disease accompanying a decreased placental blood flow, (5) the method of (3) above, wherein the disease is gestosis, (6) the method of (3) above, wherein the patient is carrying a fetus with intrauterine growth retardation, (7) the method of (4) above, wherein the disease is gestosis, (8) the method of (4) above, wherein the patient is carrying a fetus with intrauterine growth retardation, (9) use of a human-originated antithrombin-III for the manufacture of a therapeutic agent for increasing the placental blood flow,

(10) use of a human-originated antithrombin-III for the manufacture of a therapeutic agent of the diseases accompanying a decreased placental blood flow,

(11) the use of (10) above, wherein the disease is intrauterine growth retardation or gestosis, and

(12) the use of any one of (9) to (11) above, wherein the therapeutic agent is administered in a dose of 1–1,000 units/kg body weight/day.

DETAILED DESCRIPTION OF THE INVENTION

Figure 1:
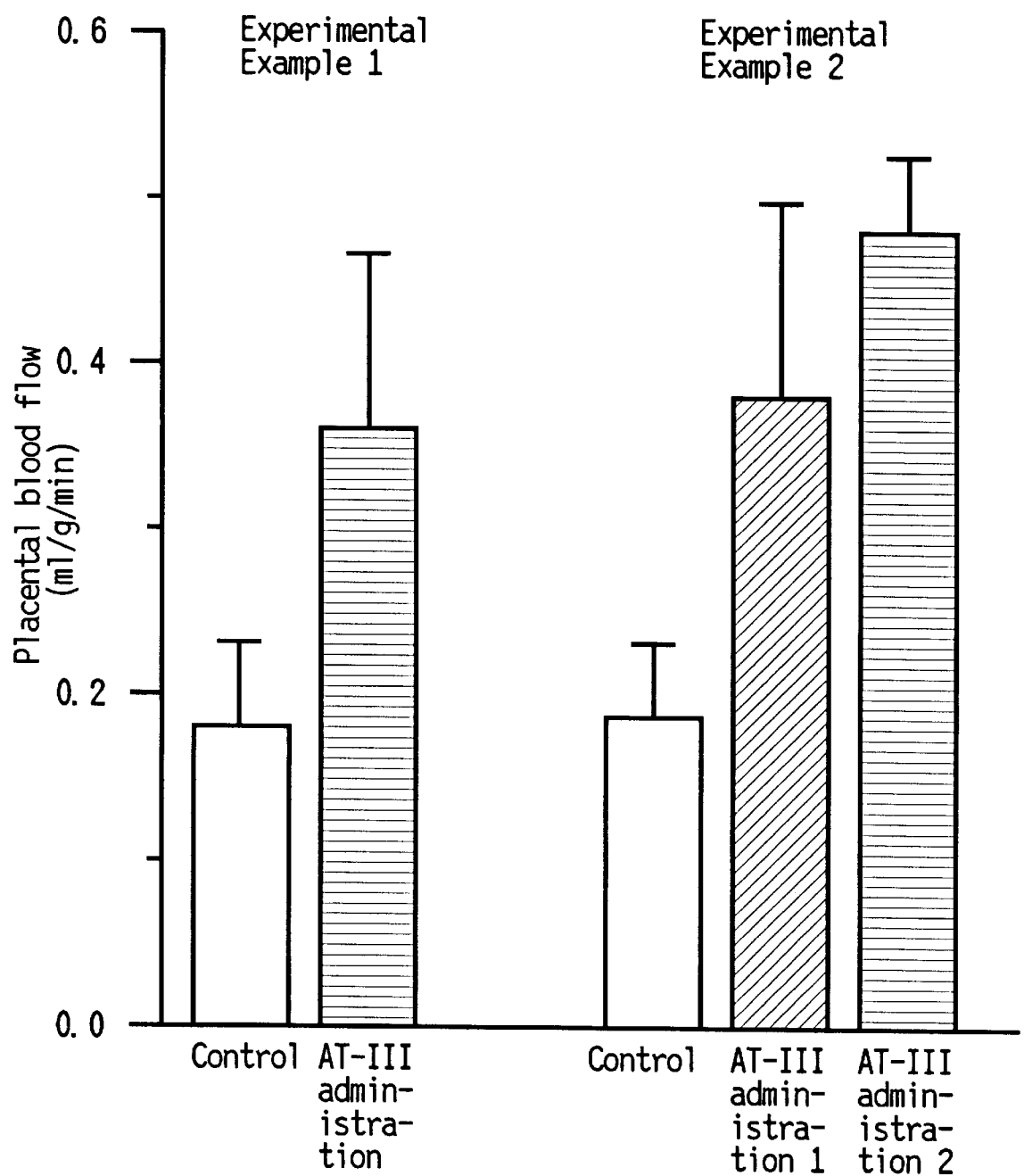
FIG. 1 is a graph showing the placental blood flow measured in Experimental Examples 1 and 2.

The AT-III to be used in the present invention is not particularly limited as long as it is human-originated and has been purified to the extent that it can be used as a pharmaceutical agent. For example, it can be purified from whole blood, blood plasma, serum or serum etc. obtained by compression of coagulated blood of human. The blood to be used preferably tests negative against HBs antigen and anti-HIV antibody, and shows not more than twice the normal value of GTP.

The starting material for preparing AT-III may be, for example, fraction IV-1 or IV, or supernatant I or II+III obtained by Cohn's fractionation of blood plasma.

AT-III can be purified by a method described in, for example, U.S. Pat No. 3,842,061 and U.S. Pat. No. 4,340,589.

AT-III can be prepared by, for example, cell culture (e.g., EP-339919), genetic engineering (e.g., EP-90505) and the like. Alternatively, a commercially available AT-III preparation such as Neuart (trademark, manufactured by The Green Cross Corporation) can be used.

The AT-III which is used as an active ingredient in the method for improving the placental blood flow of the present invention improves placental blood flow in mammals such as human, dog, cow, horse, mouse and rat, and is effective in the treatment of the diseases caused by the decreased placental blood flow, such as intrauterine growth retardation (IUGR).

The method for improving the placental blood flow of the present invention is highly safe for the fetus and mother, especially of human, since it contains human-originated AT-III as an active ingredient.

According to the method for improving the placental blood flow of the present invention, the use of AT-III increases the blood flow in the placenta, thereby normalizing the amount of the nutrition, oxygen etc. to be supplied to the fetus.

The human-originated AT-III used in the present invention may contain pharmacologically acceptable additives (e.g., carrier, excipient and diluent), stabilizers or components necessary for formulating preparations, which are generally used for pharmaceutical products, as long as it does not adversely affect the object of the present invention.

Examples of the additives and stabilizers include saccharides such as monosaccharides (e.g., glucose and fructose), disaccharides (e.g., sucrose, lactose and maltose) and sugar alcohols (e.g., mannitol and sorbitol); organic acids such as citric acid, malic acid and tartaric acid and salts thereof (e.g., sodium salt, potassium salt and calcium salt); amino acids such as glycine, aspartic acid and glutamic acid and salts thereof (e.g., sodium salt); surfactants such as polyethylene glycol, polyoxyethylene-polyoxypropylene copolymer and polyoxyethylenesorbitan fatty acid ester; heparin; and albumin.

The AT-III and the above-mentioned ingredients are admixed as appropriate to give powder, granule, tablet, capsule, syrup, injection and the like, which are administered orally or parenterally. The preferred mode is intravenous administration.

The mixture of AT-III and pharmacologically acceptable additives is preferably prepared as a lyophilized product, and dissolved when in use. Such preparation can be prepared into a solution containing about 1–100 units/ml of AT-III, by dissolving same in distilled water for injection or sterile purified water. More preferably, it is adjusted to have a physiologically isotonic salt concentration and a physiologically desirable pH value (pH 6–8).

While the dose is appropriately determined depending on symptom, body weight, sex, animal species and the like, it is generally 1–1,000 units/kg body weight/day, preferably 10–500 units/kg body weight/day of AT-III for a human adult, which is administered in one to several doses a day. In the case of intravenous administration, for example, the dose is preferably 10–100 units/kg body weight/day.

In the present specification, the titer of one unit of AT-III corresponds to that of the AT-III contained in 1 ml of normal human blood plasma.

The present invention is described in more detail in the following by illustrative Experimental Examples and Examples, to which the present invention is not limited.

EXPERIMENTAL EXAMPLE 1

(1) Test method

Wistar rats in the pregnancy of 16–20 days were anesthetized with pentobarbital (40 mg/kg) and two catheters were inserted into ventriculus sinister and right femoral artery. At least one hour after the above surgery, the rats were subjected to the following tests.

AT-III (manufactured by The Green Cross Corporation) or physiological saline (control) was bolus-administered from the tail vein in a predetermined amount shown in Table 1 below, and continuously administered at the rate shown in Table 1 for 2 hours and 5 minutes from the initiation of the administration of AT-III or physiological saline.

TABLE 1

| | bolus-administered | administration rate |
|---|---|---|
| AT-III | 300 U/kg | 75 U/kg/h |
| control | 3.3 ml/kg | 0.83 ml/kg/h |

Immediately after the completion of the administration of AT-III or physiological saline, physiological saline containing $^{57}$Co-labeled radioactive microspheres (about 100,000, diameter 15.5±0.1 μm) was injected from the ventriculus sinister. This microsphere solution was a solution of the above-mentioned microspheres homogeneously dispersed in physiological saline (0.5 ml) containing 0.01% Tween 80 by ultrasonic treatment. The arterial blood to be the control was taken from the right femoral artery at 0.458 ml/min over one minute starting from 5 seconds before the injection of the microsphere solution. Immediately after taking the control blood sample, the rats were subjected to thoracotomy and perfusation with physiological saline (250 ml). The residual blood in the blood vessels was removed to the greatest possible extent. The placenta was removed, wiped on the surface and weighed.

(2) Determination of placental blood flow

The radioactivity (CPM, counts per minute) of $^{57}$Co in the injected microsphere solution, control blood and tissue sample was counted using a γ-counter, based on which the placental blood flow was calculated from the following formula:

Placental blood flow=radioactivity (CPM) of placenta/radioactivity (CPM) of control blood×0.458 (ml/min)/weight of placenta (g)

The average (n=7) of the determined placental blood flow of the control group and the group administered with AT-III is shown in FIG. 1. The group administered with AT-III showed a remarkable increase in blood flow as compared to the control group.

EXPERIMENTAL EXAMPLE 2

(1) Test method

A plasmin inhibitor tranexamic acid (200 mg/kg) was intravenously administered to suppress fibrinolysis in the animals that underwent the same surgery as in Experimental Example 1. Then, $^{125}$I-fibrinogen (0.5 μCi) dissolved in physiological saline was intravenously administered.

Then, AT-III (manufactured by The Green Cross Corporation) or physiological saline (control) was bolus-administered from the tail vein in a predetermined amount shown in Table 2 below, and continuously administered at the rate shown in Table 2.

TABLE 2

| | bolus-administered | administration rate |
|---|---|---|
| AT-III administration 1 | 60 U/kg | 15 U/kg/h |
| AT-III administration 2 | 300 U/kg | 75 U/kg/h |
| control | 3.3 ml/kg | 0.83 ml/kg/h |

Five minutes after the initiation of the administration of AT-III or physiological saline, thromboplastin (Thromboplastin. C, manufactured by International Reagents Corporation) derived from rabbit brain was injected via the catheter inserted into ventriculus sinister at 9 ml/kg/h over one hour. The thromboplastin derived from rabbit brain was used after adjusting to a concentration of 0.48 ml/ml. The administration of AT-III or physiological saline was continued until one hour after the completion of the tissue thromboplastin administration, namely, for 2 hours and 5 minutes from the initiation of the administration of AT-III or physiological saline.

Immediately after the administration of AT-III or physiological saline, $^{57}$Co-labeled radioactive microspheres were injected as in Experimental Example 1. Thereafter, the control arterial blood was taken and the placenta was removed in the same manner as in Experimental Example 1.

(2) Determination of placental blood flow

The radioactivity of $^{125}$I and $^{57}$Co in the injected microsphere solution, control blood and tissue sample was counted using a γ-counter, based on which the placental blood flow was calculated in the same manner as in Experimental Example 1. The results are shown in FIG. 1 together with the results of Experimental Example 1. The group administered with AT-III showed a remarkable increase in blood flow as compared to the control group.

EXPERIMENTAL EXAMPLE 3

The acute toxicity ($LD_{50}$) was determined to find no difference between male and female of mouse and rat, and $LD_{50}$ was not less than 15,000 units/kg body weight for both intravenous administration and oral administration, and not less than 20,000 units/kg body weight for subcutaneous administration. In monkey (male), it was not less than 6,000 units/kg body weight by intravenous administration.

EXAMPLE 1

A paste (10 kg) of fraction IV-1 obtained by Cohn's cold alcohol fractionation was suspended in physiological saline (100 L) and barium sulfate was added to a concentration of 5% (w/v). The mixture was stirred at room temperature for 30 minutes to remove trace prothrombin by adsorption thereof to barium sulfate. The supernatant was adjusted to pH 6.5 and polyethylene glycol #4000 was added to a concentration of 13% (w/v). The resulting precipitate was removed by centrifugation. Polyethylene glycol #4000 was further added to a concentration of 30% (w/v) and the resulting precipitate was removed by centrifugation. The precipitate was dissolved in cold physiological saline (ca. 20 L) and poured onto a column packed with heparin sepharose previously adjusted with physiological saline to allow adsorption of AT-III onto the heparin sepharose column. The column was washed with an aqueous solution of 0.4M sodium chloride to remove impurity proteins. An aqueous solution of 2.0M sodium chloride was passed through the column, and the eluted fractions were recovered.

Sodium citrate was added to the aqueous solution of AT-III to a final concentration of 0.6M. The mixture was adjusted to pH 7.8 and subjected to a heat treatment at 60° C. for 10 hours. The mixture was dialyzed against 0.9% aqueous sodium chloride solution overnight to concentrate into 1% (w/v) aqueous AT-III solution, which was filtered or centrifuged as necessary to give a transparent liquid.

To this 1% (w/v) aqueous solution of AT-III were added 2% (w/v) mannitol and 0.2% (w/v) sodium citrate, and the mixture was diluted with a small amount of cold distilled water to the sodium chloride concentration of 0.5%, adjusted to pH 7.6 with 1N sodium hydroxide, sterilized by filtration through a sterile Millipore filter, dispensed by 500 units and lyophilized to give a dry preparation.

EXAMPLE 2

A lyophilized product containing, in one vial,

AT-III 500 units

Mannitol 200 mg

Sodium chloride 50 mg

Sodium citrate 52 mg was dissolved in 20 ml of distilled water for injection to give an intravenous injection.

The AT-III to be used in the present invention increases the placental blood flow in mammals and particularly improves the diseases caused by the decreased blood flow, such as intrauterine growth retardation (IUGR). According to the method for improving the placental blood flow of the present invention, the placental blood flow can be increased to be able to protect the fetus from said disease, thereby ensuring normal growth of the fetus in the body of the mother. In addition, the method for improving the placental blood flow of the present invention is highly safe to the mother and fetus, since human-originated AT-III is contained as an active ingredient. Hence, the method of the present invention can effectively and safely treat intrauterine growth retardation (IUGR) and the like.

What is claimed is:

1. A method for treating a pregnant woman who has a disease accompanying a decreased placental blood flow and who is carrying a fetus with intrauterine growth retardation which comprises increasing placental blood flow by administering a human antithrombin-III to said woman in an amount effective for treating the intrauterine growth retardation.

2. The method of claim 1 wherein the antithrombin-III is administered in a dose of 1–1,000 units/kg body weight/day.

* * * * *